United States Patent [19]

Parker

[11] Patent Number: 4,725,663

[45] Date of Patent: Feb. 16, 1988

[54] USE OF N-GLYCIDYL BENZOXAZOLES AS LATENTLY CROSS-LINKABLE REACTIVE DILUENTS FOR EPOXY RESINS

[75] Inventor: Theodore L. Parker, Lafayette, Calif.

[73] Assignee: The Dow Chemical Company, Midland, Mich.

[21] Appl. No.: 947,204

[22] Filed: Dec. 29, 1986

Related U.S. Application Data

[62] Division of Ser. No. 745,178, Jun. 17, 1985, abandoned.

[51] Int. Cl.$^4$ .............................................. C80G 59/02
[52] U.S. Cl. ................................. 528/103; 528/109; 528/117; 528/369
[58] Field of Search ................ 528/103, 109, 117, 369

[56] References Cited

U.S. PATENT DOCUMENTS 4,631,331 12/1986 Parker .................................. 528/117
4,631,332 12/1986 Parker .................................. 528/117

OTHER PUBLICATIONS

Lespagnol et al., Chem. Abst. 74-87877r.
Aflyatunova et al., Chem. Abst. 84-135529.
Lee and Neville, *The Handbook of Epoxy Resins*, pp. 13-7 to 13-9.

*Primary Examiner*—John Kight
*Assistant Examiner*—Frederick F. Krass

[57] ABSTRACT

N-glycidyl derivatives of certain benzo-N-heterocycles, such as 2-(3H)-benzoxazolone, may be employed as latently cross-linkable reactive diluents for epoxy resins.

20 Claims, No Drawings

USE OF N-GLYCIDYL BENZOXAZOLES AS LATENTLY CROSS-LINKABLE REACTIVE DILUENTS FOR EPOXY RESIN

This is a divisional of application Ser. No. 745,178, filed June 17, 1985, now abandoned.

BACKGROUND OF THE INVENTION

N-substituted derivatives of benzoxazolones and sulfur-containing analogues thereof are known. However, it is believed that no N-glycidyl derivatives of these benzoheterocycles have been made or proposed. The N-methyl derivative of 2-(3H)-benzothiazolone has been converted to the hydrazone, which has utility as a colorimetric analytical reagent. 2-(3H)-benzothiazolthione, as such, has utility as a vulcanization accelerator. Otherwise, as far as is known to the present inventor, nothing relevant to the possible utility of the N-glycidyl derivatives has been disclosed in the literature.

OBJECTS OF THE INVENTION

The primary object of the present invention is to provide a type of mono-epoxide which—as an adduct with an active hydrogen compound—will rearrange to provide a phenolic hydroxyl function.

Another object is to provide a unique type of reactive diluent which is latently cross-linkable.

A further object is to provide a type of monoepoxide which, with the aid of an initiator, can act as a monomer for the production of highly novel, essentially linear polymers made up of alternating phenylene and 5-membered heterocyclic ketone or thione moieties, connected through —O—$CH_2$— or —S—$CH_2$— links.

An additional object is to provide polymers of the latter type.

It is also an object to provide processes for the preparation of the foregoing monomers and polymers.

Still other objects will be made apparent to those knowledgeable in the art by the following specifications and claims.

SUMMARY OF THE INVENTION

It has been found that the foregoing objects can be attained by (1) reacting epibromohydrin with a benzoheterocycle of the formula

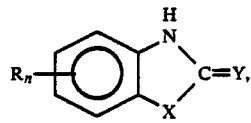

wherein R is a non-interfering substituent the same or different in each occurrence, n is 0, 1 or 2 and X and Y, independently, are O or S, in the presence of a base; and (2) causing the resulting N-glycidyl derivative to react—with the help of an initiator—with itself or with an epoxy resin and a compound containing two functions reactive with oxirane groups.

The N-glycidyl compounds of the invention may be represented by the formula

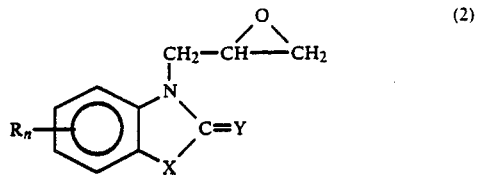

wherein R, n, X and Y are as above defined with regard to formula (1).

The adducts of the N-glycidyl compounds with initiators, $ZH_a$, may be represented by the formula

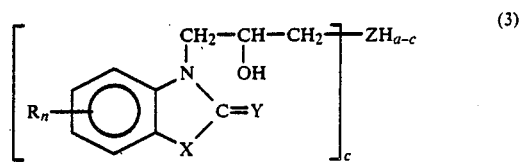

wherein Z is the residue of the active hydrogen compound, preferably a difunctional cross-linker for epoxy resins, a is 1, 2 or more, preferably 1 or 2, c is at least 1 and R, n, X and Y are as above defined.

The adducts of formula (3) can be rearranged (by heating and/or catalysis) to novel phenols or thiophenols of the following formula:

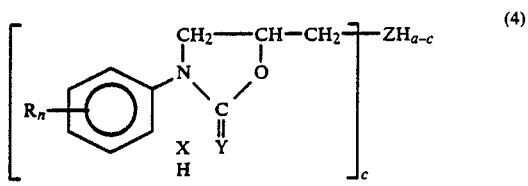

The homopolymers are produced by (a) one to one reaction of molecules of formula (4) with molecules of formula (2) to form phenols or thiophenols of the following formula:

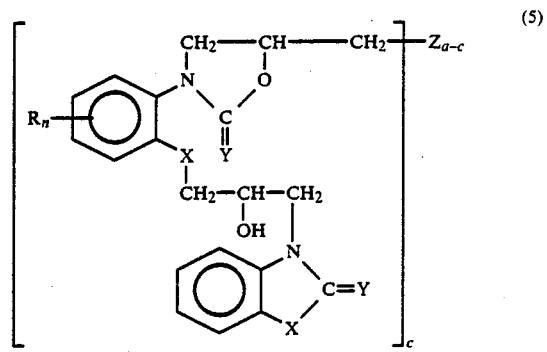

which in turn rearrange in the same manner as molecules of formula (3) do, to form phenols or thiophenols analogous to those of formula (4), and (b) reaction of the latter phenols with more molecules of formula (2), etc.; the resulting homopolymer being represented by the following formula:

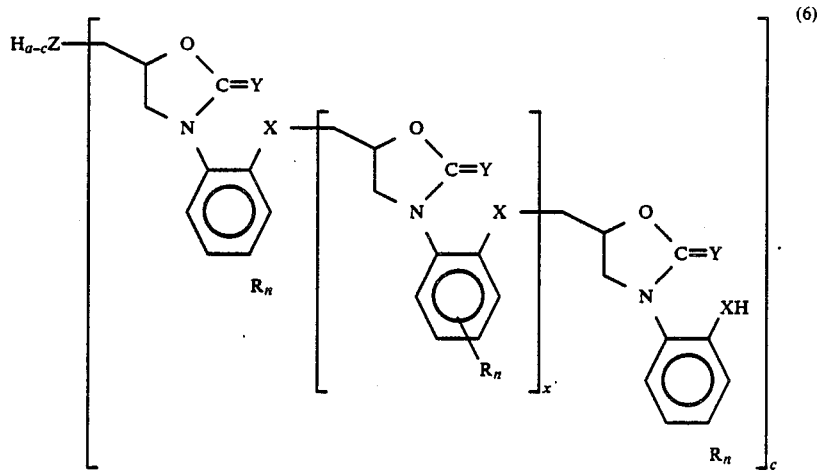

wherein x is an integer.

The N-glycidyl compounds of formula (2) may be mixed with an epoxy resin (having an average oxirane functionality greater than 1), thereby substantially decreasing the viscosity of the resin. An epoxy cross-linker and a difunctional initiator (which may be the same as the cross-linker) may then be mixed in and the resulting mixture heated just enough to cause adduction of the initiator with the N-glycidyl oxirane group and rearrangement of the adduct to a phenol or thiophenol of formula (4). The rearranged adduct will then include two oxirane-reactive groups and, upon further heating, will react—as a modified version of the cross-linker—with the epoxy resin, thereby curing the same.

DETAILED DESCRIPTION

The compounds of formula (1) which are suitable for the practice of the present invention may be grouped into four types; 2-(3H)-benzoxazolones, -benzoxazolthiones, benzothiazolones and -benzothiazolthiones.

The benzoxazolones are exemplified by 2-(3H)-benzoxazolone itself, the compound of formula (1) in which n=zero, X=O and Y=O. This compound ($C_7H_5NO_2$; mol. wt. 135.118) melts at 141°-2° C. and forms a stable monohydrate which melts at 97°-8° C. Also, the 6-methoxy derivative is known.

The benzoxazolthiones are exemplified by 2-(3H)-benzoxazolthione itself, the compound of formula (1) in which n=zero, X=O and Y=S. This compound ($C_7H_5NOS$; mol. wt. 151.183) melts at 170° C., forms a monohydrochloride which melts at 196° C., and is the major tautomer of 2-mercapto-benzoxazole.

The benzothiazolones are exemplified by 2-(3H)-benzothiazolone itself, the compound of formula (1) in which n=zero, X=S and Y=O. This compound ($C_7H_5NOS$; mol. wt. 151.183) melts at 128° C. (136° C.) and is the major tautomer of 2-hydroxy-benzothiazole.

The benzothiazolthiones are exemplified by 2-(3H)-benzothiazolthione itself, the compound of formula (1) in which n=zero, X=S and Y=S. This compound ($C_7H_5NS_2$; mol. wt. 167.250) melts at 177°-9° C. (It is a neoplastic agent and emits highly toxic fumes when decomposed.) Also, the 6-nitro derivative is known.

In those compounds of formula (1) in which n is 1 or 2, each R is a substituent which is feasible to incorporate in the molecule and which does not interfere, to an intolerable extent, with the reactions in the sequence required for the preparation of at least one of the compounds of formulas (2), (3), (4), (5) or (6). The following R-groups are representative of those considered to be non-interfering: chloro, bromo, nitro, lower alkoxy, phenoxy, lower alkyl or alkenyl, $C_6$–$C_{10}$ aryl, aralkyl or alkaryl and lower alkylthio. n preferably is 1 (most preferably 0).

Those compounds of formula (1) meeting the preceding two requirements can be prepared by reaction of the corresponding mono- or disubstituted, orthohydroxy or -mercapto aniline with phosgene, thiophosgene or trichloromethyl chloroformate ("diphosgene" or "liquid phosgene"; available from Morton Thiokol Inc.).

Preparation of Compounds of Formula (2)

The reaction between the compound of formula (1) and epibromohydrin preferably is carried out with the neat reactants but an inert solvent may be employed if necessary. The mole ratio of the epibromohydrin to the benzo compound can range from about 2/1 to about 20/1 but preferably is within the range of from about 7 to about 10. The base is employed in a ratio of from about 1 to 1.25 mols per mol of the benzo compound, preferably about 1.02–1.10, and may be any of the bases typically employed in the preparation of glycidyl ethers from epihalohydrins. NaOH is the preferred base and is conveniently employed as 20–30 wt. % aqueous NaOH. Alternatively, a finely divided solid base, such as $CaCO_3$, may be employed as a dispersion in a highly stirred reaction mixture. Reaction temperatures of from room temperature up to about 125° are considered suitable; temperatures of 100° or less—particularly when the benzo compound is a benzothiazolthione—are preferred. Suitable reaction times range from several days (at 30° C.) to about 15 minutes (at 125° C.). The final reaction mixture may be worked up in accordance with any conventional practice designed to separate organic solvent-soluble from water-soluble products and more volatile from less volatile materials.

The reaction of the N-glycidyl derivatives of formula (2) with initiators can be carried out with the neat reactants or in the presence of an inert solvent (or an epoxy resin). Suitable initiators are mono- or polyfunctional active hydrogen compounds which will adduct with oxirane groups predominantly to form a secondary alcoholic hydroxyl on the center carbon of the glycidyl moiety backbone. These include glycols, bases and acids, of the types generally used to initiate polyglycol formation from alkylene oxides. Also suitable, however, are compounds comprising reactive methylol groups; most notably, for example, N-methylol groups in aminoplast resins, such as are commonly employed as cross-linkers for epoxies. Phenols—including polyfunctional mononuclear phenols and bis-phenols—are also suitable initiators. A particularly suitable phenol for use as an initiator is a preformed compound of formula (4).

Reaction conditions and work-up procedures conventionally employed for reactions of active hydrogen compounds with epoxides are generally suitable for the formation and recovery of the adducts of fromula (3).

The rearrangement of the compounds of formula (3) to the corresponding compounds of formula (4) may be carried out in the absence of epoxides if isolation of the resulting phenol is desired. It has been found that the rearrangement is catalyzed by compounds, such as tetrabutyl phosphonium acetate or an imidazole/metal salt complex for example, known to catalyze the advancement of epoxy resins with bis-phenols. Accordingly, high temperatures are not required for the rearrangement and ordinary to moderately elevated temperatures are preferred.

If the rearrangement is not carried out in situ, i.e., starting with the precursor compound of formula (3) in admixture with a phenol-reactive material (such as an epoxide, for example), the resulting phenol may be isolated (by conventional work-up procedures). In general, however, in situ rearrangement in the presence of an epoxide (the corresponding glycidyl ether of formula (2), when production of a homopolymer of formula (5) is desired) is preferred. In the latter case, the rearrangement product will be a transient, intermediate species—as will the one-to-one reaction product (formula 5) of the latter species with a molecule of formula (2).

A preferred option, when the initiator is a crosslinker for epoxies, is to pre-react the N-glycidyl compound (formula (2)) with a sufficient excess of the initiator so that c (in formulas (3) and (4)) is less than a and the phenol obtained as the rearrangement product retains at least one of the cross-linking functions of the initiator, thereby still being at least difunctional and capable of functioning as a cross-linker. The resulting mixture of modified and unmodified cross-linker molecules can then be employed in the usual manner to cure epoxy resins of various types. In this option, the initiator/N-glycidyl compound adduct has been rearranged, and the phenolic hydroxyl is no longer latent. In the opposite situation, the N-glycidyl compound or, preferably, the adduct (formula (3)), is mixed with the epoxide and is a latent phenolic until rearranged in situ.

With regard to the homopolymers of formula (6), it may be noted that each oxazolone (or analogous) group includes a reactive carbonyl (or thiocarbonyl) function which can undergo a variety of reactions typical of ketones (and thiones—since the usual dimerization reactions of thiones may be somewhat hindered by the bulk of the polymer molecule), thus permitting facile and substantial modification of the properties of the polymer (as to strength of H bonding with other species, for example).

EXAMPLES

The following examples are for purposes of illustration and are not to be construed as limiting the present invention in a manner inconsistent with the claims in this patent.

Example 1

Preparation of N-glycidyl Derivative of 2-(3H)-Benzoxazolone ("Benzoxazolone epoxide"; $C_{10}H_9NO_3$, Mol. wt. 191.18)

A solution of 2-benzoxazolone, 1.35 g, 0.01 mole, in epibromohydrin, 13.5 g, 0.10 mole, 10:1 equivalent ratio, was stirred until homogeneous, then heated to 100° C. A solution of NaOH, 0.42 g, 0.0105 mole, in water, 1.26 g, was added in small portions evenly over 30 minutes to the stirred reaction mixture. After all the caustic solution (25 wt. % NaOH) had been added, the mixture was held at 100° C. for an additional 30 minutes; then 20 ml water and 20 ml methyl ethyl ketone were added. The phases were allowed to separate, the lower brine layer discarded, and the organic layer dried with anhyd. $MgSO_4$ and filtered. Solvent and the remaining epibromohydrin were removed by vacuum distillation on a rotoevaporator at 100° C., to yield a dark viscous oil which partially crystallized on cooling; 1.65 g, 86% of theory. The product had an epoxide equivalent weight (EEW) of 199 (theory is 191).

The product, a viscous oil at ambient temperature, has a tendency to crystallize on prolonged standing and has the emperical formula $C_{10}H_9NO_3$.

Example 2

Larger Scale Preparation of Benzoxazolone Epoxide

To a 2-liter, 3-necked, round-bottomed flask fitted with a mechanical stirrer, a heat controller thermocouple probe and a reflux condenser, was added 67.5 grams (0.5 mole) of 2-benzoxazolone and 480 grams (3.5 moles) of epibromohydrin. The flask contents were stirred and heated to 80° C.; 10 ml of water were added and then about 2 ml of 25% aqueous NaOH—without noticeable effect. Dropwise addition of more 25% NaOH was started. When the pot temperature reached 105° C., the addition was stopped until the temperature dropped to 100°. Addition was then resumed. Before the addition of the base (final total about 10 ml) was complete (about 25 minutes) it was necessary to heat to hold a temperature of 80° C.—which was maintained for another hour. 100 ml of water was stirred in and phase separation allowed to occur. The organic phase was separated, dried over anhyd. $MgSO_4$, filtered and stripped in vacuo to a pot temperature of 150° C. The residue was a dark oil, 88.5 grams (92.7% of theoretical yield) which was found to have an EEW of 230 (vs. 191 for the desired product). When poured on metal foil and allowed to cool, the oil changed to a sticky resin which crystallized to a solid mass over a period of several hours. The melting range of the solid was 73°–78° C.

Example 3

Effect of Benzoxazolone Epoxide on Melt Viscosity of a Complex, Latently Cross-linkable Epoxy Resin The temperature/viscosity profile of a 13 gram portion of the product of Example 2 was determined, using a Brookfield bobbin viscometer with the controller programmed for a temperature ramp rate of about 10° C. per minute, over the range of 80°–125° C. (A #21 bob was used, at 100 rpm.) The temperature/viscosity results are given in Table 1:

TABLE 1

| TEMP. (°C.) | 80 | 90 | 95 | 100 | 110 | 125 |
| --- | --- | --- | --- | --- | --- | --- |

TABLE 1-continued

| VISCOSITY (Centipoises) | 22.5 | 16.0 | 14.0 | 10.0 | 7.5 | 5.0 |

The complex epoxy resin (an embodiment of a separate invention by the present inventor) was formed by reacting 0.722 gram equiv. of tris-(p-glycidyloxyphenyl)methane with 0.722 gram moles of 2-(3H)benzoxazolone at about 150° C. and mixing the hot product with another 0.633 g. equiv. of the tris-compound and 0.543 g. equiv. of a partially hydrolyzed, slightly advanced diglycidyl ether of bisphenol A. The resulting resin had a Mettler softening point of 86° C.

The latter resin was mixed with successively greater amounts of the benzoxazolone epoxide and the viscosity of each mixture determined (with the same apparatus described above) at 100° C. and at 110° C., as noted in Table 2 following.

TABLE 2

| Wt. Ratio Epoxy Resin to Benzoxazolone Epoxide | Temperature °C. | Shear Rate RPM | Viscosity in Centipoises |
|---|---|---|---|
| 100/0 | 100 | 5 | 31600 |
|  | 110 |  | 13750 |
| 95/5 | 100 |  | 18250 |
| 90/10 | 100 |  | 9700 |
|  | 110 | 10 | 3900 |
| 85/15[1] | 100 | 5 | 7100 |
|  | " | 10 | 7175 |
|  | " | 20 | 7200 |
|  | 110 | 10 | 2375 |
|  | " | 20 | 2400 |
|  | " | 80 | 2435 |
|  | " | 100 | 2430 |

NOTE:
[1]Mettler softening point 69.5° C.

The mole ratios predicted (from a semi-log plot of the foregoing data) for a viscosity of 2500 cps were 76/24 (at 100° C.) and 86/14 (at 110° C.).

Example 4

Homopolymerization of Benzoxazolone Epoxide

A brittle, cross-linked solid was obtained by mixing the epoxide with cyclohexylamine (5 wt. % of the mixture), as an initiator and 0.5% of tetrabutyl phosphonium acetate (as a catalyst) and heating.

Example 5

(A) Essentially in the manner of Example 2, the following N-glycidyl derivatives of the corresponding 2-(3H)benzoheterocycles are prepared.

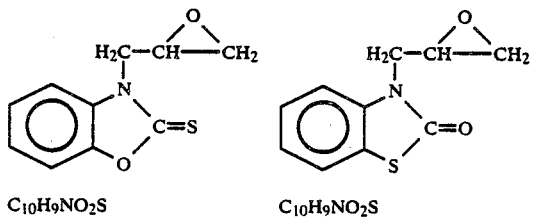

$C_{10}H_9NO_2S$
M = 207.245

$C_{10}H_9NO_2S$
M = 207.245

-continued $C_{10}H_9NOS_2$
M = 223.312

$C_{10}H_8ClNO_3$
M = 225.632

$C_{10}H_7Br_2NO_2S$
M = 365.069

$C_{11}H_{10}NO_3S$
M = 237.271

(B) Essentially in the manner of Example 4, homopolymers and/or copolymers are prepared by reacting each of the latter six compounds with itself and/or with at least one other thereof.

Example 6

Mixtures of one or more of the N-glycidyl derivatives of Examples 2 and 5(A) with each of a variety of resins which are di- to tetra(glycidyloxyphenyl)alkanes and/or linear polyether polyhydroxy diepoxides, in derivative to resin weight ratios of from about 15/85 to about 25/75, are found to exhibit considerably lower melt viscosities than the resins or resin mixtures per se and to be curable with conventional epoxy curing agents to thermoset products largely retaining the chemical and physical properties of the resins per se, cured with the same agents.

It should be noted that the compounds of formula (2) have utility as intermediates for the preparation of biologically active reaction products of the oxirane moieties in the glycidyl groups with a variety of oxirane-reactive compounds.

It should also be noted that, in formulas (3)–(6), Z may be either an organic or inorganic radical and has a valence equal to a.

What is claimed is:

1. An epoxy composition comprising an epoxy resin and, as a laterally cross-linkable, reactive diluent therefor, an N-glycidyl compound of the formula

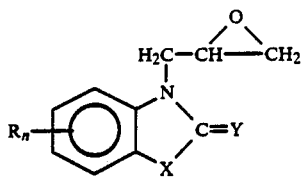

wherein
R, independently in each occurrence, is halo, nitro, lower alkoxy, phenoxy, lower alkyl or alkenyl, $C_6$-$C_{10}$ aryl, aralkyl or aralkyl or lower alkylthio;
X and Y, independently are O or S; and
n is zero, one or two.

2. The composition of claim 1 in which n, in said compound, is zero or one.

3. The composition of claim 2 in which n is zero.

4. The composition of claim 3 in which Y, in said formula, is 0.

5. The composition of claim 4 in which, in said formula, each of X and Y is 0; i.e., said compound is 2-(3-glycidyl)benzoxazolone.

6. The composition of claim 1 additionally comprising an active hydrogen compound, $ZH_a$, capable of forming an adduct with said N-glycidyl compound, said adduct being of the formula

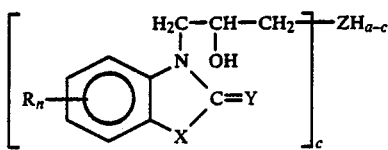

wherein a is one or more; c is at least one, and Z is a radical having a valence equal to a.

7. The composition of claim 6 wherein, in said active hydrogen compound, a is one or two.

8. The composition of claim 7 wherein a is one.

9. The composition of claim 6 wherein a equals two and $ZH_a$ is a cross-linker for epoxy resins.

10. The composition of claim 6, 7, 8 or 9 additionally comprising a catalytically effective amount of a catalyst for the rearrangement of said adduct to a phenol of the formula

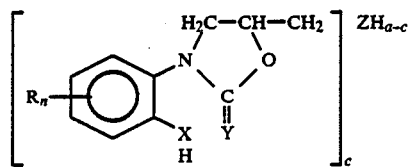

11. The composition of claim 1, 2, 3, 4, 5, 6, 7, 8 or 9 wherein said epoxy resin is a di- to tetra(glycidyloxyphenyl)alkane or a linear polyether polyhydroxy diepoxide.

12. The method of curing an epoxy composition, said composition comprising an epoxy resin, an N-glycidyl compound of the formula

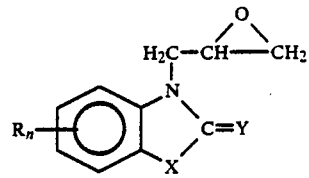

and an active hydrogen compound, $ZH_a$, wherein Z is a radical of valence a and a is one or more;
and said method comprising
(a) causing said active hydrogen compound to react with said N-glycidyl compound to form an adduct of the formula

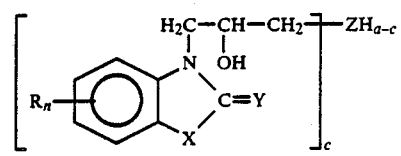

wherein c is at least one;
(b) causing said adduct to rearrange to a phenol of the formula

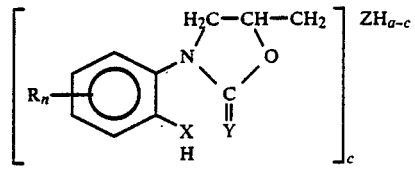

and
(c) subjecting said composition to sufficient heat for a sufficient period of time to cure it.

13. The method of claim 12 wherein a is one or two.

14. The method of claim 13 wherein a is one.

15. The method of claim 13 wherein a is two and $ZH_a$ is a cross-linker for said epoxy resin.

16. The method of claim 12, 13, 14 or 15 wherein said rearrangement is effected by heating of said composition.

17. The method of claim 12, 13, 14 or 15 wherein said rearrangement is effected by adding to said composition a catalytically effective amount of a rearrangement catalyst and heating as may be necessary.

18. The cured product of the method of claim 16.

19. The cured product of the method of claim 17.

20. The composition of claim 6, cured in the form of a shaped article.

* * * * *

UNITED STATES PATENT AND TRADEMARK OFFICE
CERTIFICATE OF CORRECTION

PATENT NO. : 4,725,663
DATED : February 16, 1988
INVENTOR(S) : Theodore L. Parker Page 1 of 2

It is certified that error appears in the above-identified patent and that said Letters Patent is hereby corrected as shown below:

Col. 2, lines 33-40, change formula to read as follows:

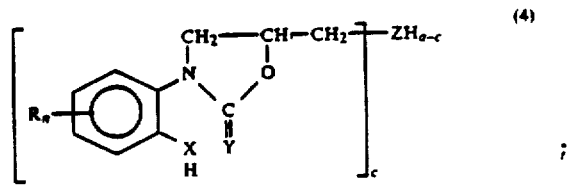

Col. 3, lines 1-20, change formula to read as follows:

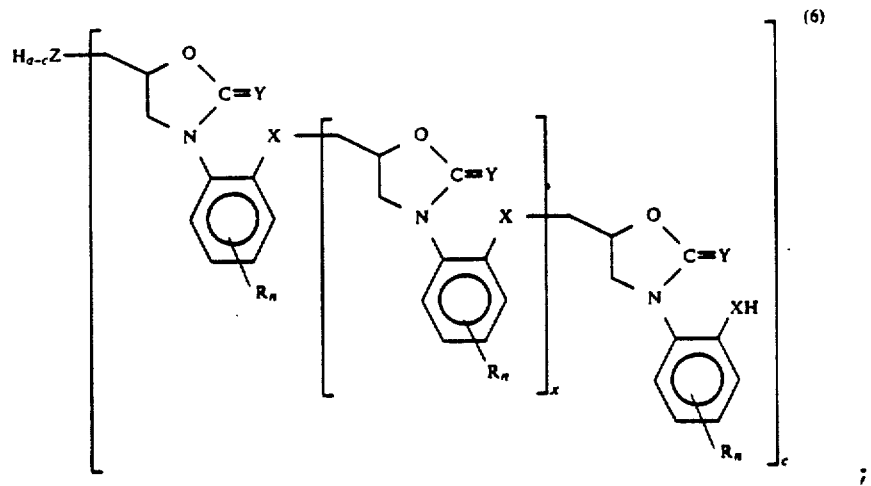

UNITED STATES PATENT AND TRADEMARK OFFICE
CERTIFICATE OF CORRECTION

PATENT NO. : 4,725,663

DATED : February 16, 1988

INVENTOR(S) : Theodore L. Parker

It is certified that error appears in the above-identified patent and that said Letters Patent is hereby corrected as shown below:

Col. 5, line 12, "formula" has been misspelled.

Signed and Sealed this

Twenty-fourth Day of January, 1989

Attest:

DONALD J. QUIGG

*Attesting Officer*  Commissioner of Patents and Trademarks